(12) United States Patent
Guilani et al.

(10) Patent No.: US 9,796,561 B2
(45) Date of Patent: Oct. 24, 2017

(54) WEAR DETECTION FOR COATED BELT OR ROPE

(75) Inventors: Brad Guilani, Woodstock Valley, CT (US); Hong Yang, Avon, CT (US)

(73) Assignee: OTIS ELEVATOR COMPANY, Farmington, CT (US)

( * ) Notice: Subject to any disclaimer, the term of this patent is extended or adjusted under 35 U.S.C. 154(b) by 118 days.

(21) Appl. No.: 14/376,983

(22) PCT Filed: Feb. 7, 2012

(86) PCT No.: PCT/US2012/024043
§ 371 (c)(1),
(2), (4) Date: Aug. 6, 2014

(87) PCT Pub. No.: WO2013/119203
PCT Pub. Date: Aug. 15, 2013

(65) Prior Publication Data
US 2015/0015280 A1    Jan. 15, 2015

(51) Int. Cl.
*G01R 27/08* (2006.01)
*B66B 7/12* (2006.01)
(Continued)

(52) U.S. Cl.
CPC .............. *B66B 7/1223* (2013.01); *B66B 1/24* (2013.01); *B66B 5/0025* (2013.01);
(Continued)

(58) Field of Classification Search
CPC ......... B66B 7/1223; B66B 7/062; B66B 7/06; B66B 1/24; B66B 1/145; B66B 5/02;
(Continued)

(56) References Cited

U.S. PATENT DOCUMENTS 5,834,942 A    11/1998  De Angelis
6,289,742 B1    9/2001  De Angelis
(Continued)

FOREIGN PATENT DOCUMENTS

CN    101977834 A    2/2011
CN    102115991 A    7/2011
(Continued)

OTHER PUBLICATIONS

State Intellectual Property Office of People's Republic China Search Report; Application No. 201280069270.7; Mailing Date: Dec. 2, 2015; 2 pages.
(Continued)

*Primary Examiner* — Thang Le
(74) *Attorney, Agent, or Firm* — Cantor Colburn LLP

(57) ABSTRACT

A method of wear detection of a coated belt or rope includes connecting a wear detection unit to one or more monitoring strands and/or cords of a coated belt or rope. The coated belt or rope includes one or more baseline strands and/or cords exhibiting a first change in electrical resistance as a function of bending cycles of the belt or rope and one or more monitoring strands and/or cords exhibiting a second change in electrical resistance as a function of bending cycles of the belt or rope, greater than the first change in electrical resistance. An electrical resistance of the one or more monitoring strands and/or cords is measured via the wear detection unit. Using at least the measured electrical resistance of the one or more monitoring strands and/or cords, a wear condition of the belt or rope is determined.

12 Claims, 9 Drawing Sheets

(51) Int. Cl.
*D07B 1/14* (2006.01)
*D07B 1/16* (2006.01)
*G01M 5/00* (2006.01)
*B66B 1/24* (2006.01)
*B66B 5/00* (2006.01)
*B66B 5/02* (2006.01)
*B66B 7/06* (2006.01)
*B66B 9/00* (2006.01)
*G01N 27/04* (2006.01)
*G01N 27/20* (2006.01)
*D07B 1/22* (2006.01)

(52) U.S. Cl.
CPC .............. *B66B 5/0031* (2013.01); *B66B 5/02* (2013.01); *B66B 7/06* (2013.01); *B66B 7/062* (2013.01); *B66B 9/00* (2013.01); *D07B 1/145* (2013.01); *D07B 1/162* (2013.01); *G01M 5/0025* (2013.01); *G01M 5/0033* (2013.01); *G01M 5/0083* (2013.01); *G01N 27/041* (2013.01); *G01N 27/20* (2013.01); *D07B 1/22* (2013.01); *D07B 2201/1014* (2015.07); *D07B 2201/2044* (2013.01); *D07B 2501/2007* (2013.01); *Y10T 428/2933* (2015.01)

(58) Field of Classification Search
CPC .... B66B 5/0025; B66B 5/0031; G01N 27/20; G01N 27/041
USPC ......... 324/699, 693; 187/266, 390–393, 276, 187/375
See application file for complete search history.

(56) References Cited

U.S. PATENT DOCUMENTS

| | | | | |
|---|---|---|---|---|
| 7,540,359 B2* | 6/2009 | Veronesi | ................. | B66B 7/062 187/247 |
| 8,171,713 B2* | 5/2012 | Gilmore | ................. | D02G 3/047 57/244 |
| 9,327,941 B2* | 5/2016 | Dold | ................. | B66B 7/1223 |
| 2002/0108814 A1* | 8/2002 | Pitts | ................. | B66B 19/02 187/254 |
| 2003/0011483 A1* | 1/2003 | Lamb | ................. | B66B 7/1223 340/664 |
| 2003/0150167 A1* | 8/2003 | Bourgois | ................. | E05F 11/481 49/352 |
| 2004/0046540 A1* | 3/2004 | Robar | ................. | B66B 7/1223 324/71.2 |
| 2008/0081721 A1* | 4/2008 | Bissig | ................. | D07B 1/025 474/260 |
| 2008/0149430 A1 | 6/2008 | De Angelis | | |
| 2011/0284331 A1* | 11/2011 | Stucky | ................. | B66B 7/1223 187/393 |
| 2012/0061188 A1* | 3/2012 | Aulanko | ................. | B66B 7/1261 187/254 |

FOREIGN PATENT DOCUMENTS

| | | |
|---|---|---|
| EP | 1795483 A1 | 6/2007 |
| JP | 976709 A | 3/1997 |
| JP | 2003268685 A | 9/2003 |
| JP | 2006028671 A | 2/2006 |
| JP | 2008303493 A | 12/2008 |
| KR | 10-2006-0097072 A | 9/2006 |
| WO | 2009090299 A1 | 7/2009 |
| WO | 2011004071 A2 | 1/2011 |
| WO | 2013070224 A1 | 5/2013 |

OTHER PUBLICATIONS

Supplementary European Search Report; Application No. 12867921.4; Dated: Jan. 19, 2016; 10 pages.

Notification of Transmittal of the International Search Report and the Written Opinion of the International Searching Authority, or the Declaration; PCT/US2012/024043; Oct. 27, 2010; 8 pages.

European Office Action and Communication; Application No. 12867921.4; Dated Jan. 13, 2017; 5 pages.

* cited by examiner

WEAR DETECTION FOR COATED BELT OR ROPE

BACKGROUND OF THE INVENTION

The subject matter disclosed herein relates to coated belts or ropes used, for example, in elevator systems. More specifically, the subject disclosure relates to wear detection (e.g. of corrosion, fretting, etc.) of coated belts or ropes used for elevator suspension and/or driving.

Elevator systems utilize ropes or belts operably connected to an elevator car, and routed over one or more sheaves, also known as pulleys, to propel the elevator car along a hoistway. Coated steel belts in particular include a plurality of wires located at least partially within a jacket material. The plurality of wires is often arranged into one or more strands and the strands are then arranged into one or more cords. In an exemplary belt construction, a plurality of cords is typically arranged equally spaced within a jacket in a longitudinal direction.

During normal elevator operation, coated steel belts are subjected to a large number of bending cycles as the belt travels over drive sheaves and deflector sheaves of the elevator system. These bending cycles cause a degradation of the breaking strength of the wires or cords within the coated steel belt via the mechanism of wire fretting or fatigue. Such fatigue is a major contributor to reduction in service life of the coated steel belt. While the service life of the coated steel belt can be estimated through calculation, a more accurate estimation of remaining life of the coated steel belt is often obtained by utilizing a life-monitoring system.

One such system is called resistance-based inspection (RBI). An RBI system is secured to the belt at a fixed point of the elevator system and monitors an electrical resistance of each cord in the belt. Since the electrical resistance of each cord is proportional to its cross-sectional area, changes is electrical resistance can be correlated to reduction in cross-sectional area of the cord, indicating an amount of fretting of the cord, and a corresponding remaining service life. Some cord configurations, however, do not exhibit a significant, measurable change in resistance which can be correlated to a number of bending cycles or cord degradation. In such cases, assessment of belt condition based upon changes in electrical resistance of the cords is difficult due to the small magnitude of change in electrical resistance of the cords as the cords wear.

BRIEF DESCRIPTION OF THE INVENTION

According to one aspect of the invention, a coated belt or rope includes a plurality of wires arranged into a plurality of strands and/or cords. The plurality of stands and/or cords include one or more baseline stands and/or cords exhibiting a first change in electrical resistance as a function of bending cycles of the belt or rope and one or more monitoring stands and/or cords exhibiting a second change in electrical resistance as a function of bending cycles of the belt, greater than the first change in electrical resistance. A jacket substantially retains the plurality of strands and/or cords.

Alternatively in this or other aspects of the invention, a monitoring strand and/or cord of the one or more monitoring strands and/or cords is located at an outer position.

Alternatively in this or other aspects of the invention, the belt or rope is a belt, and a monitoring cord of the one or more monitoring cords is located at a longitudinally outer position in the belt.

Alternatively in this or other aspects of the invention, a monitoring strand and/or cord of the one or more monitoring strands and/or cords is located at a center position.

Alternatively in this or other aspects of the invention, the belt or rope is a belt, and a monitoring cord of the one or more monitoring cords is located at a longitudinally center position of the belt.

Alternatively in this or other aspects of the invention, the one or more monitoring strands and/or cords are at least two monitoring strands and/or cords.

Alternatively in this or other aspects of the invention, two monitoring strands and/or cords of the at least two monitoring stands and/or cords are located adjacently.

Alternatively in this or other aspects of the invention, the belt or rope is a belt, and two monitoring cords of the at least two monitoring cords are located longitudinally adjacently in the belt.

Alternatively in this or other aspects of the invention, a monitoring strand and/or cord of the one or more monitoring stands and/or cords has a substantially same wire cross-sectional area as a baseline strand and/or cord of the one or more baseline stands and/or cords.

According to another aspect of the invention, an elevator system includes an elevator car, one or more sheaves, a wear detection unit, and a coated belt or rope including a plurality of wires arranged into a plurality of strands and/or cords. The plurality of stands and/or cords include one or more baseline stands and/or cords exhibiting a first change in electrical resistance as a function of bending cycles of the belt or rope and one or more monitoring stands and/or cords exhibiting a second change in electrical resistance as a function of bending cycles of the belt, greater than the first change in electrical resistance. A jacket substantially retains the plurality of strands and/or cords. The belt or rope is operably connected to the wear detection unit.

Alternatively in this or other aspects of the invention, the wear detection unit measures electrical resistance of the one or more monitoring cords.

Alternatively in this or other aspects of the invention, the wear detection unit is disposed at an upper end of an elevator hoistway.

According to another aspect of the invention, a method of wear detection of a coated belt or rope includes connecting a wear detection unit to one or more monitoring strands and/or cords of a coated belt or rope. The coated belt or rope includes one or more baseline strands and/or cords exhibiting a first change in electrical resistance as a function of bending cycles of the belt or rope and one or more monitoring strands and/or cords exhibiting a second change in electrical resistance as a function of bending cycles of the belt or rope, greater than the first change in electrical resistance. An electrical resistance of the one or more monitoring strands and/or cords is measured via the wear detection unit. Using at least the measured electrical resistance of the one or more monitoring strands and/or cords, a wear condition of the belt or rope is determined.

Alternatively in this or other aspects of the invention, the determining step includes determining the change in electrical resistance of the one or more monitoring strands and/or cords.

Alternatively in this or other aspects of the invention, the determining step includes determining an increase in electrical resistance.

Alternatively in this or other aspects of the invention, the change in electrical resistance is compared to a threshold and action is taken if the threshold is exceeded.

Alternatively in this or other aspects of the invention, taking action comprises one or more of sounding an alarm or stopping operation of the elevator system.

Alternatively in this or other aspects of the invention, continuity of at least one of the baseline strands is monitored.

The detailed description explains the invention, together with advantages and features, by way of examples with reference to the drawings.

DETAILED DESCRIPTION OF THE INVENTION

Figure 1A:
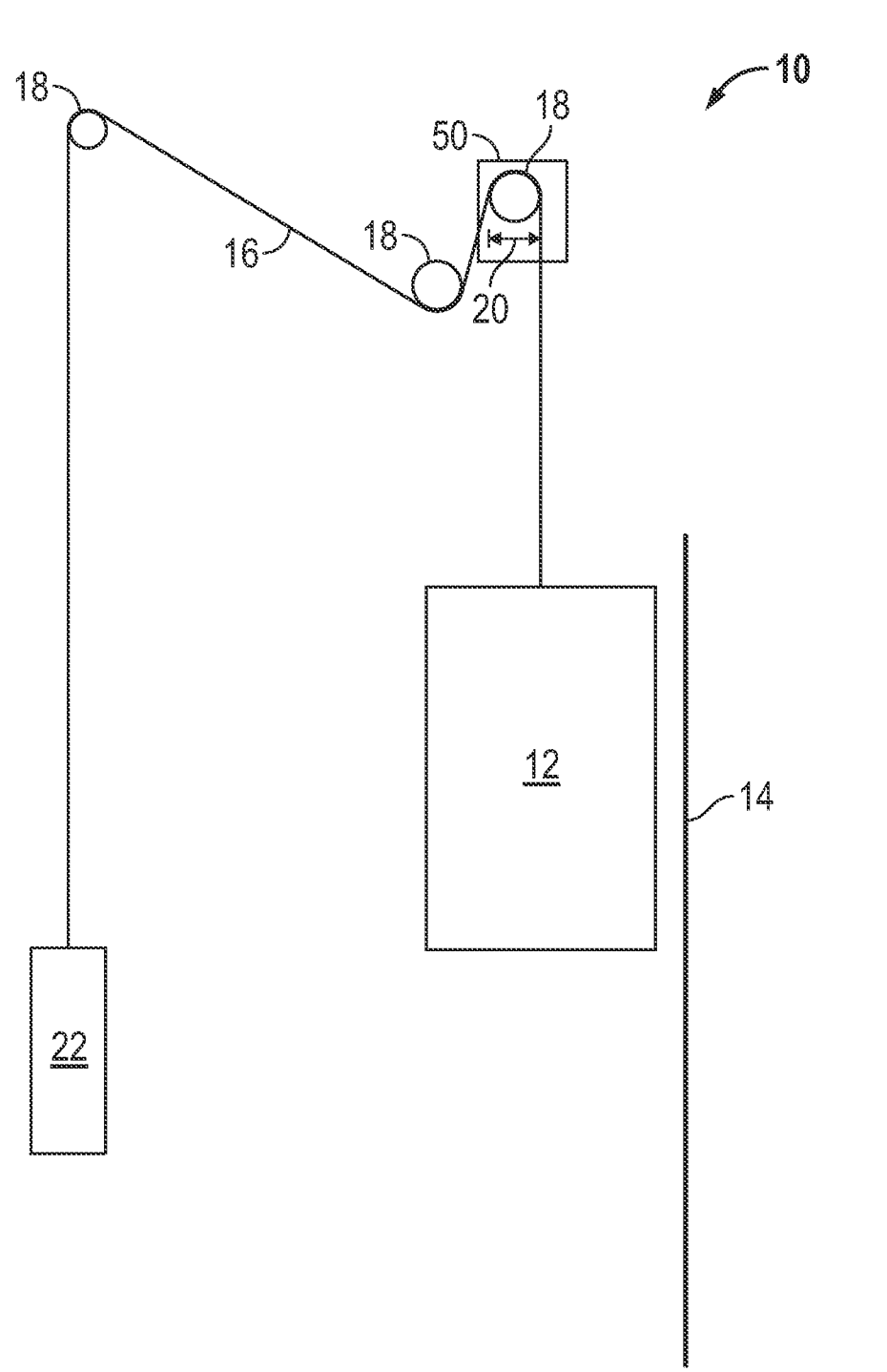
FIG. 1A is a schematic of an exemplary elevator system having a 1:1 roping arrangement.
Figure 1B:
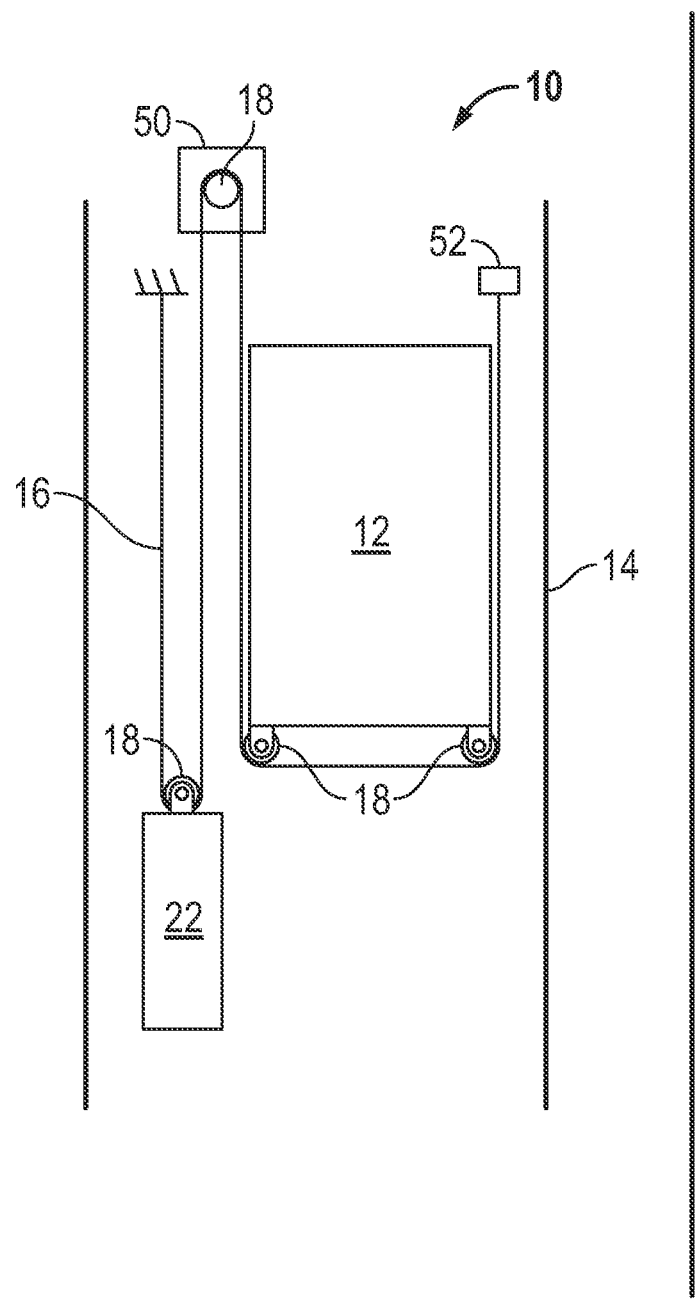
FIG. 1B is a schematic of another exemplary elevator system having a different roping arrangement.
Figure 1C:
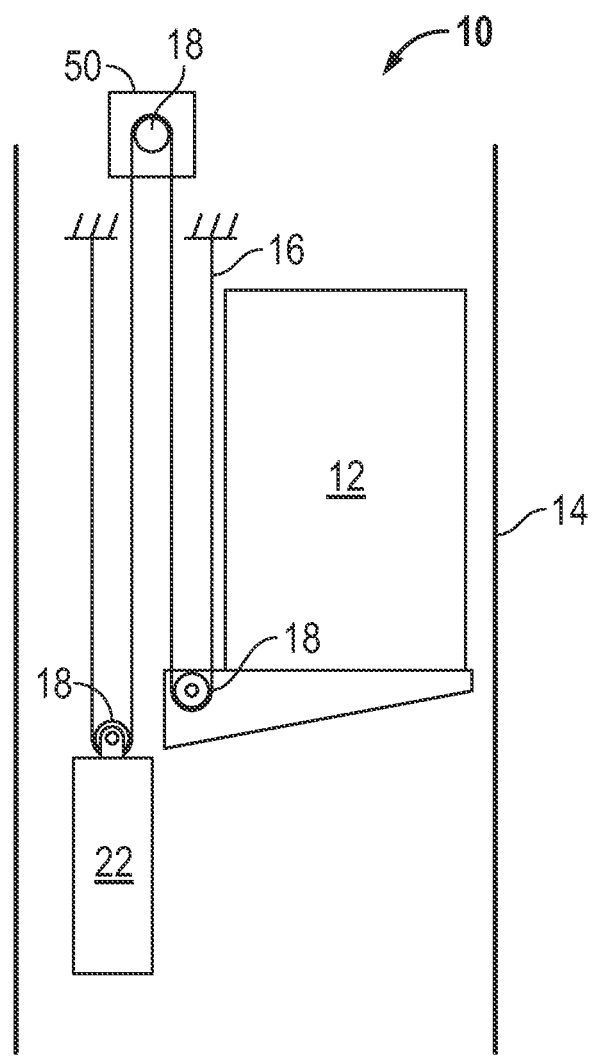
FIG. 1C is a schematic of another exemplary elevator system having a cantilevered arrangement.

Shown in FIGS. 1A, 1B and 1C are schematics of exemplary traction elevator systems 10. Features of the elevator system 10 that are not required for an understanding of the present invention (such as the guide rails, safeties, etc.) are not discussed herein. The elevator system 10 includes an elevator car 12 operatively suspended or supported in a hoistway 14 with one or more belts 16. The one or more belts 16 interact with one or more sheaves 18 to be routed around various components of the elevator system 10. The one or more belts 16 could also be connected to a counterweight 22, which is used to help balance the elevator system 10 and reduce the difference in belt tension on both sides of the traction sheave during operation.

The sheaves 18 each have a diameter 20, which may be the same or different than the diameters of the other sheaves 18 in the elevator system 10. At least one of the sheaves 18 could be a drive sheave. A drive sheave is driven by a machine 50. Movement of the drive sheave by the machine 50 drives, moves and/or propels (through traction) the one or more belts 16 that are routed around the drive sheave.

At least one of the sheaves 18 could be a diverter, deflector or idler sheave. Diverter, deflector or idler sheaves are not driven by a machine 50, but help guide the one or more belts 16 around the various components of the elevator system 10. Further, one or more of the sheaves 18, such as the diverter, deflector or idler sheaves, may have a convex shape or crown along its axis of rotation to assist in keeping the one or more belts 16 centered, or in a desired position, along the sheaves 18.

In some embodiments, the elevator system 10 could use two or more belts 16 for suspending and/or driving the elevator car 12. In addition, the elevator system 10 could have various configurations such that either both sides of the one or more belts 16 engage the one or more sheaves 18 (such as shown in the exemplary elevator systems in FIG. 1A, 1B or 1C) or only one side of the one or more belts 16 engages the one or more sheaves 18.

FIG. 1A provides a 1:1 roping arrangement in which the one or more belts 16 terminate at the car 12 and counterweight 22. FIGS. 1B and 1C provide different roping arrangements. Specifically, FIGS. 1B and 1C show that the car 12 and/or the counterweight 22 can have one or more sheaves 18 thereon engaging the one or more belts 16 and the one or more belts 16 can terminate elsewhere, typically at a structure within the hoistway 14 (such as for a machineroomless elevator system) or within the machine room (for elevator systems utilizing a machine room). The number of sheaves 18 used in the arrangement determines the specific roping ratio (e.g., the 2:1 roping ratio shown in FIGS. 1B and 1C or a different ratio). FIG. 1C also provides a cantilevered type elevator. The present invention could be used on elevator systems other than the exemplary types shown in FIGS. 1A, 1B and 1C.

Figure 2A:
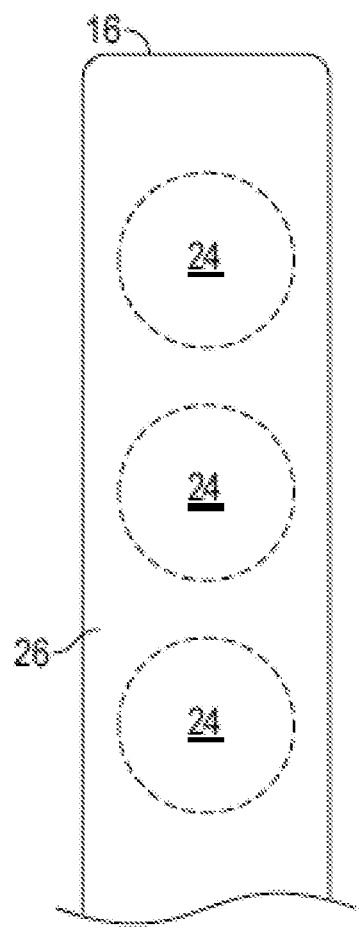
FIG. 2A is a cross-sectional view of a prior art elevator belt.

FIG. 2A provides a schematic of a prior art belt construction or design. Each belt 16 is constructed of a plurality of wires (e.g. twisted into one or more strands and/or cords 24) in a jacket 26. As seen in FIG. 2, the belt 16 has an aspect ratio greater than one (i.e. belt width is greater than belt thickness). The belts 16 are constructed to have sufficient flexibility when passing over the one or more sheaves 18 to provide low bending stresses, meet belt life requirements and have smooth operation, while being sufficiently strong to be capable of meeting strength requirements for suspending and/or driving the elevator car 12. The jacket 26 could be any suitable material, including a single material, multiple materials, two or more layers using the same or dissimilar materials, and/or a film. In one arrangement, the jacket 26 could be a polymer, such as an elastomer, applied to the cords 24 using, for example, an extrusion or a mold wheel process. In another arrangement, the jacket 26 could be a woven fabric that engages and/or integrates the cords 24. As an additional arrangement, the jacket 26 could be one or more of the previously mentioned alternatives in combination.

The jacket 26 can substantially retain the cords 24 therein. The phrase substantially retain means that the jacket 26 has sufficient engagement with the cords 24 to transfer torque from the machine 50 through the jacket 26 to the cords 24 to drive movement of the elevator car 12. The jacket 26 could completely envelop the cords 24 (such as shown in FIG. 2A), substantially envelop the cords 24, or at least partially envelop the cords 24.

Figure 3:
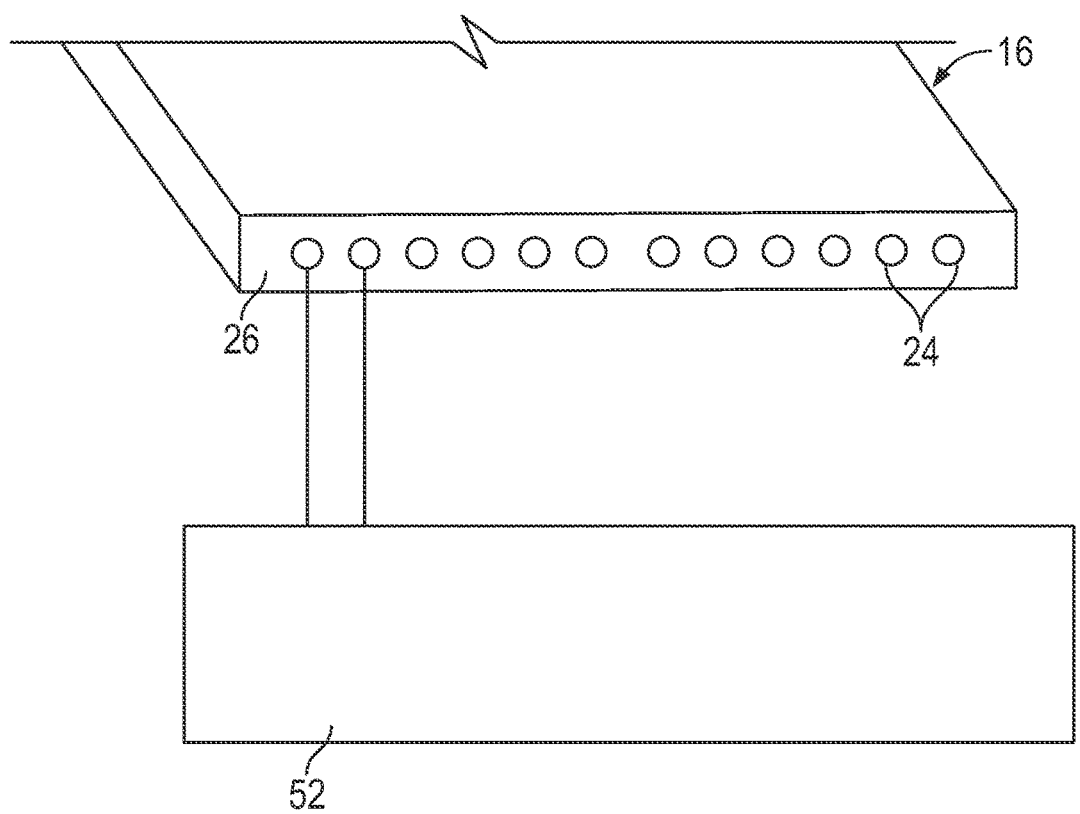
FIG. 3 is a schematic of an elevator belt wear detection unit.

Referring to FIG. 3, a wear detection unit 52 is electrically connected to one or more cords 24 of the belt 16. The wear detection unit 52 is connected to a terminated portion of the belt 16, for example, at an end of the belt 16 located at an upper end of the hoistway 14. It is to be appreciated, though, that this location is merely exemplary and other locations for connecting the wear detection unit 52 to the belt 16 are contemplated within the present scope. During operation, an electrical current is applied through the cords 24. A resulting voltage allows for determination of an electrical resistance of the cord 24. This measured resistance is compared to an initial resistance of the cord. A change in the electrical resistance of the cord 24, typically an increase in resistance, indicates wear the cord 24. The change in resistance is compared to a threshold change value, and when the threshold change value is exceeded, action may be taken by the elevator system 10, including but not limited to, sounding of an alarm or stopping operation of the elevator system 10.

As stated above, in some belts 16, a magnitude of change in resistance of the cords 24 is not significant as a function of bending cycles of the belt 16. To make assessment of these belts 16 via the wear detection unit 52 more effective, the belt 16 is configured with one or more cords 24a with a different construction than baseline cords 24b. The cords 24a, hereinafter referred to as "monitoring cords" 24a, are constructed such that a change in electrical resistance in the monitoring cords 24a, as a function of bending cycles of the belt 16, is significantly greater than the resistance change of baseline cords 24b. Both the monitoring cords 24a and baseline cords 24b can be load carrying cords. In other words, neither the monitoring cords 24a nor the baseline cords 24b are intended to be sacrificial cords.

Figure 4:
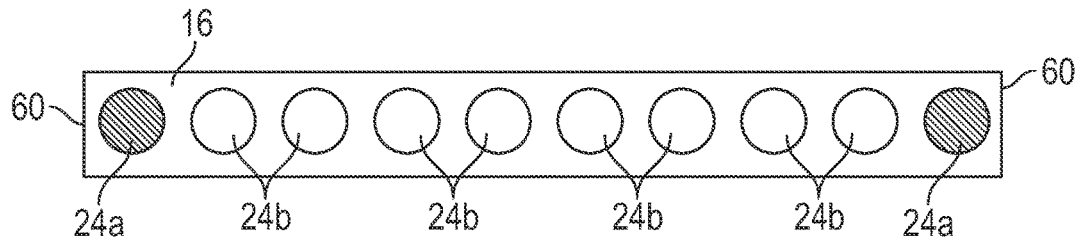
FIG. 4 is a cross-sectional view of an embodiment of an elevator belt.
Figure 5:
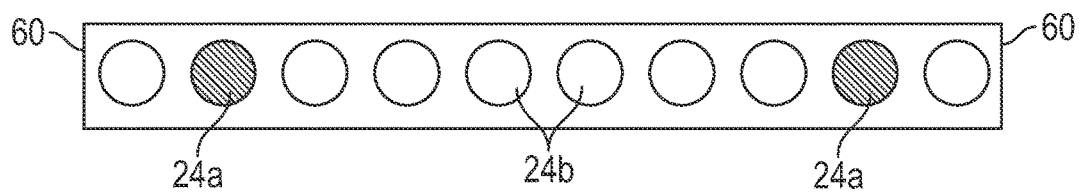
FIG. 5 is a cross-sectional view of another embodiment of an elevator belt.
Figure 6:
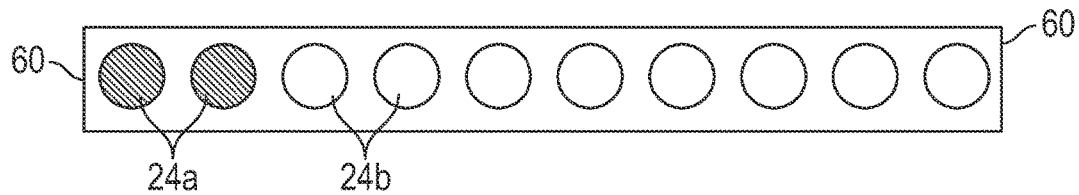
FIG. 6 is a cross-sectional view of another embodiment of an elevator belt.
Figure 7:
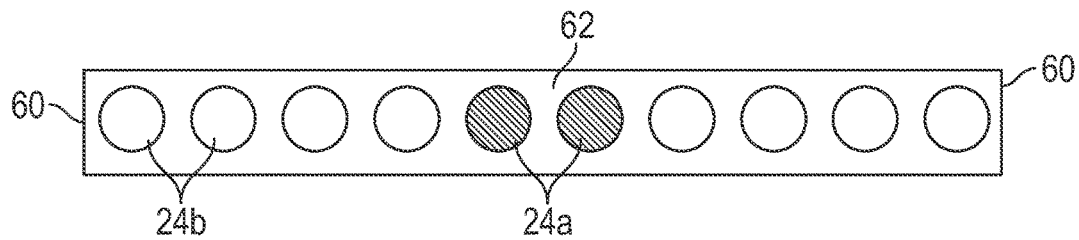
FIG. 7 is a cross-sectional view of another embodiment of an elevator belt.

Wear detection and assessment is performed on the monitoring cords 24a, with a correlation determined between a change in resistance of the monitoring cords 24a and the belt 16 as a whole. Any number of monitoring cords 24a may be included in the belt 16, with example belt 16 configurations shown in FIGS. 4-7. In FIGS. 4-7, the belts 16 are ten-cord belts 16 having varying numbers of monitoring cords 24a in varying locations in the belts 16. While ten-cord belts 16 are shown, it is to be appreciated that belts 16 with other numbers of cords, for example, six, eight or twelve cords, may be utilized in the implementation of the subject matter disclosed herein. In FIG. 4, the belt 16 includes two monitoring cords 24a located in longitudinally outer locations 60 in the belt 16, with the remaining cords comprising baseline cords 24b. Referring to FIG. 5, the monitoring cords 24a may be located inboard of the longitudinally outer position, while in FIG. 6, the monitoring cords 24a may be located in adjacent positions at one longitudinal end 60 of the belt 16. Referring now to FIG. 7, the monitoring cords 24a may be located at the longitudinally center positions 62 in the belt. It is to be appreciated that the configurations shown and described herein are merely exemplary and that other belt 16 configurations are contemplated by the present disclosure.

Figure 8:
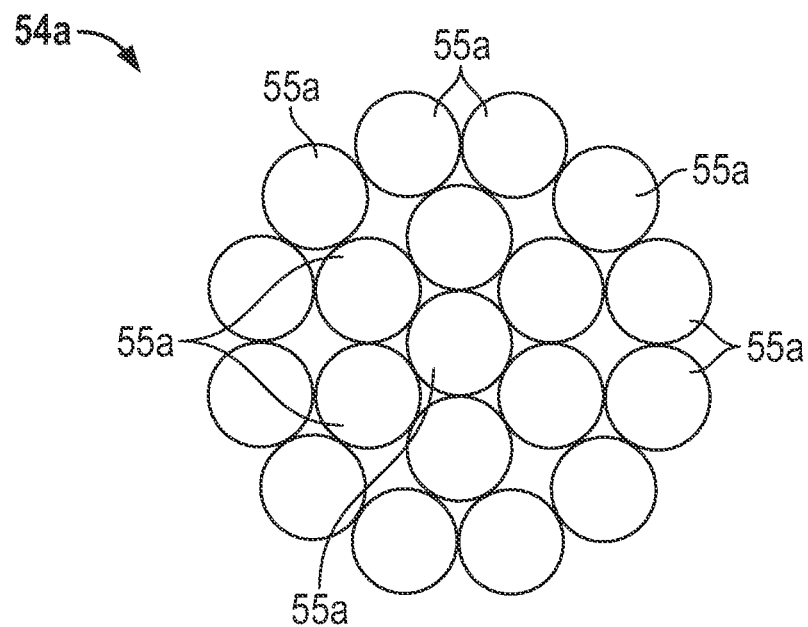
FIG. 8 is a cross-sectional view of an embodiment of a baseline strand used in a baseline cord and a monitoring strand used in a monitoring cord for an elevator belt.
Figure 8:
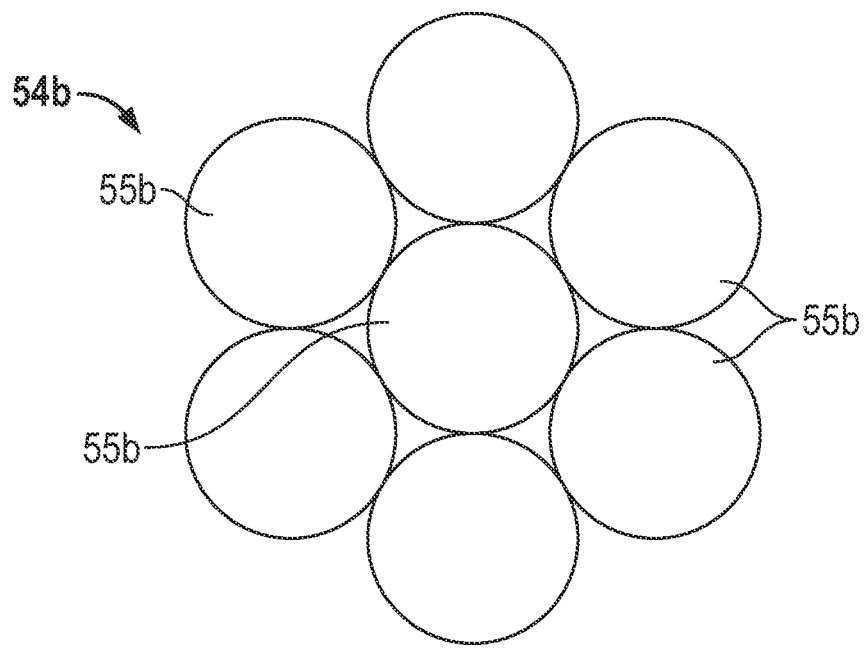
Figure 9:
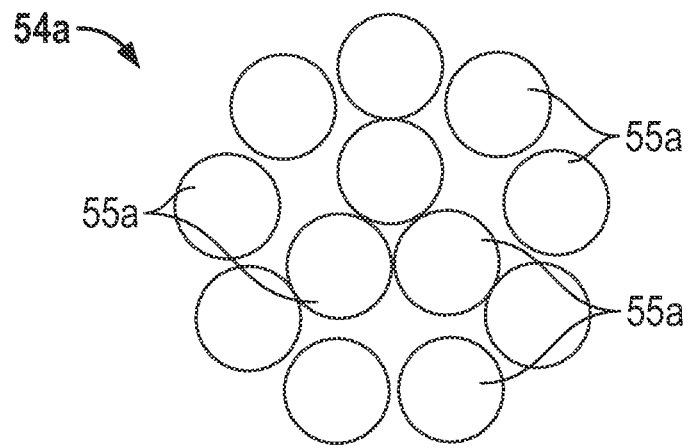
FIG. 9 is a cross-sectional view of another embodiment of a monitoring strand used a monitoring cord for an elevator belt and the baseline strand from FIG. 8.
Figure 9:
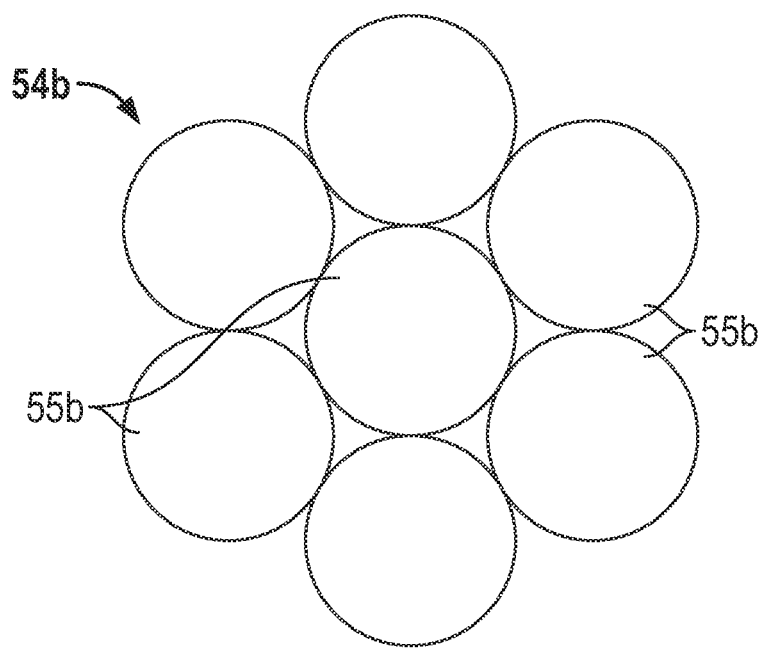

Monitoring cords 24a may achieve their greater change in resistance relative to the baseline cords 24b in a variety of ways. Referring to FIG. 8, for example, the baseline cord 24b may be a 7×7 cord, with seven strands 54b each including seven wires 55b. As an example, 0.30 mm and 0.34 mm diameter wires 55b form 0.94 mm strands 54b that form the 2.95 mm diameter cord 24b. A monitoring cord 24a for the same belt 16 may be formed from smaller diameter wires 55a, which exhibit higher change of resistance per belt 16 bending cycle. To achieve a breaking strength that is equivalent to that of the baseline cord 24b (e.g. between about −25% and +10% of the breaking strength), the monitoring cord 24a could be a 7×19 cord, with seven strands 54a each including nineteen wires 55a (e.g. in a 1+6+12 arrangement). As an example, 0.20 mm wires 55a form 1.0 mm strands 54a that form the 3.0 mm diameter cord 24a. As another possible alternative, and as shown in FIG. 9, the monitoring cord 24a could be a 7×12 cord, with seven strands 54a each including twelve wires 55a (e.g. in a 3+9 arrangement). As an example, 0.245 mm wires 55a form 0.98 mm strands 54a that form the 2.94 mm diameter cord 24a. In such arrangements, the monitoring cord 24a may include substantially the same cross-sectional area of wires 55a as the baseline cord 24b. In other embodiments, the cross-sectional area of the monitoring cord 24a may be within about +/−10% of the cross-sectional area of the baseline cord 24b. Other configurations, such as those where the monitoring cords 24a have more wires per cord than the baseline cords 24b, for example, 50% or more wires per cord, are contemplated within the scope of the present disclosure. Thus the breaking strength of the monitoring cord 24a is substantially equivalent to that of the baseline cord 24b, while having a greater change in resistance per bending cycle of the belt 16.

Although the description above discusses the monitoring of the resistance of the monitoring cords 24a for wear and not the baseline cords 24b, it is still within the scope of this invention that some monitoring of the baseline cords 24b could also occur. For example, the baseline cords 24b could be monitored for continuity (e.g. to determine whether cord breakage has occurred).

Figure 2B:
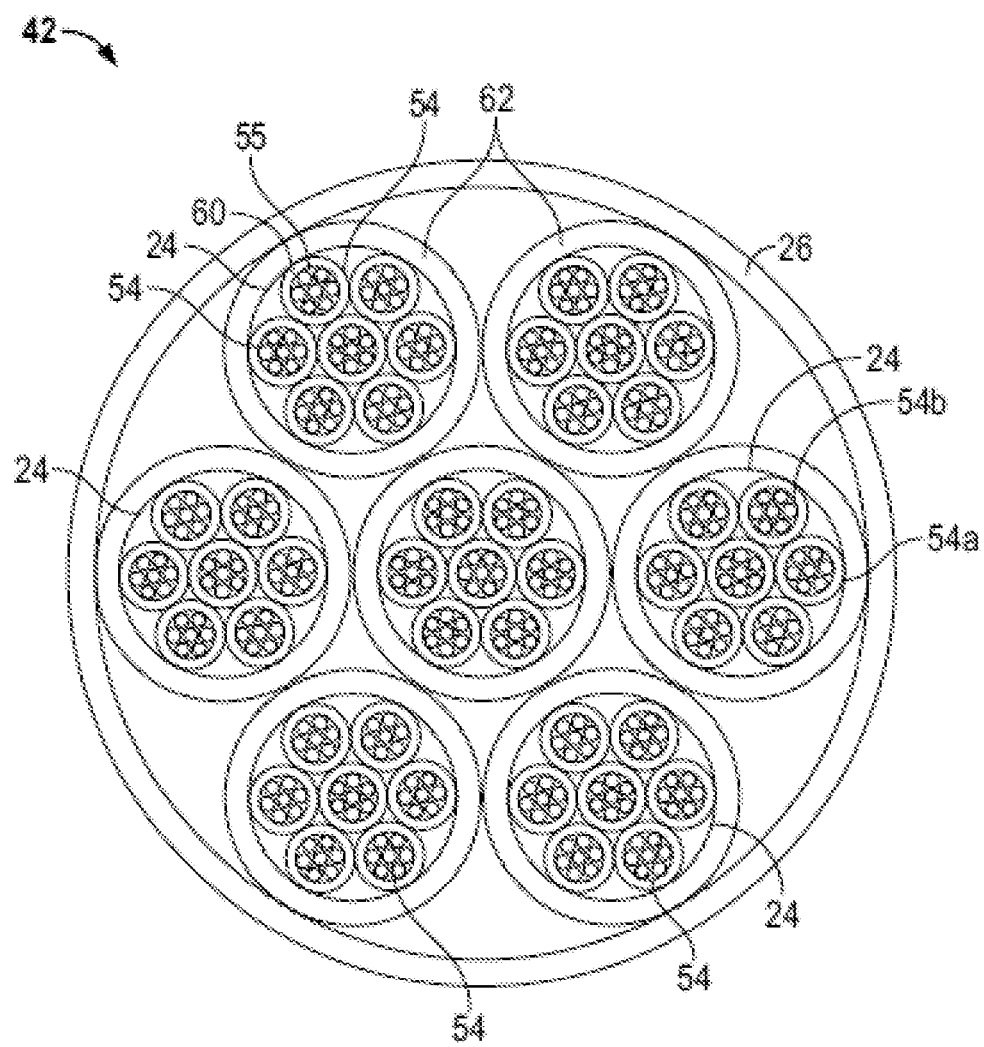
FIG. 2B is a cross-sectional view of a prior art elevator rope.

Alternatively, referring now to FIG. 2B, the elevator car 12 may be suspended or supported in the hoistway 14 with one or more coated ropes 42 formed from a plurality of wires 55 formed into a plurality of strands 54 and/or cords 24. The wires 55, strands 54 or cords 24 are twisted into a compact, stable, and in some embodiments, substantially circular shape, and coated in a jacket 26. In some embodiments, before forming the rope 42, individual strands 54 and/or cords 24 may be coated in a strand jacket 60 and/or a cord jacket 62, respectively. Similar to the belt 16 described above, the rope 42 includes monitoring strands 54a and baseline strands 54b in one or more of the cords 24, and monitoring may be performed substantially in a similar manner to that described above.

During operation, an electrical current is applied through the monitoring strands 54a within the rope 42. A resulting voltage allows for determination of an electrical resistance of the monitoring strands 54a. This measured resistance is compared to an initial resistance of the monitoring strands 54a. A change in the electrical resistance of the monitoring strands 54a, typically an increase in resistance, indicates wear of wires 55a within the monitoring strand 54a. The change in resistance is compared to a threshold change value, and when the threshold change value is exceeded, action may be taken by the elevator system 10, including but not limited to, sounding of an alarm or stopping operation of the elevator system 10.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

The invention claimed is:
1. A coated belt or a coated rope, comprising:
  a plurality of wires arranged into a plurality of strands or cords, the plurality of strands or cords including:
    one or more baseline strands or baseline cords exhibiting a first change in electrical resistance as a function of bending cycles of the belt or rope; and one or more monitoring strands or monitoring cords exhibiting a second change in electrical resistance as a function of bending cycles of the belt, greater than the first change in electrical resistance; and a jacket substantially retaining the plurality of strands or cords;

wherein the one or more monitoring strands or monitoring cords are formed from smaller diameter wires than the diameter of wires forming the one or more baseline strands or baseline cords, the one or more monitoring strands or monitoring cords having a monitoring breaking strength in the range of −25% to +10% relative to a baseline breaking strength of the one or more baseline strands or baseline cords.

2. The belt or the rope of claim 1, wherein a monitoring strand or a monitoring cord of the one or more monitoring strands or monitoring cords is disposed at an outer position.

3. The belt or the rope of claim 2, wherein the belt or rope is a belt, and a monitoring cord of the one or more monitoring cords is disposed at a longitudinally outer position in the belt.

4. The belt or the rope of claim 1, wherein a monitoring strand or a monitoring cord of the one or more monitoring strands or monitoring cords is disposed at a center position.

5. The belt or the rope of claim 4, wherein the belt or rope is a belt, and a monitoring cord of the one or more monitoring cords is disposed at a longitudinally center position of the belt.

6. The belt or the rope of claim 1, wherein the one or more monitoring strands or monitoring cords are at least two monitoring strands or monitoring cords.

7. The belt or the rope of claim 6, wherein two monitoring strands or monitoring cords of the at least two monitoring stands or monitoring cords are disposed adjacently.

8. The belt or the rope of claim 7, wherein the belt or rope is a belt, and two monitoring cords of the at least two monitoring cords are disposed longitudinally adjacently in the belt.

9. The belt or the rope of claim 1, wherein a monitoring strand or monitoring cord of the one or more monitoring stands or monitoring cords has a substantially same wire cross-sectional area as a baseline strand or a baseline cord of the one or more baseline stands or baseline cords.

10. An elevator system comprising:

an elevator car;

one or more sheaves;

a wear detection unit; and a belt or a rope operably connected to the wear detection unit, including:

a plurality of wires arranged into a plurality of strands or cords, the plurality of strands or cords including:

one or more baseline strands or baseline cords exhibiting a first change in electrical resistance as a function of bending cycles of the belt or rope; and one or more monitoring strands or monitoring cords exhibiting a second change in electrical resistance as a function of bending cycles of the belt, greater than the first change in electrical resistance; and a jacket substantially retaining the plurality of strands or cords;

wherein the one or more monitoring strands or monitoring cords are formed from smaller diameter wires than the diameter of wires forming the one or more baseline strands or baseline cords, the one or more monitoring strands or monitoring cords having a monitoring breaking strength in the range of −25% to +10% relative to a baseline breaking strength of the one or more baseline strands or baseline cords.

11. The elevator system of claim 10, wherein the wear detection unit measures electrical resistance of the one or more monitoring cords.

12. The elevator system of claim 10, wherein the wear detection unit is disposed at an upper end of an elevator hoistway.

* * * * *